US006773939B1

(12) United States Patent
Wright (10) Patent No.: US 6,773,939 B1
(45) Date of Patent: Aug. 10, 2004

(54) METHOD AND APPARATUS FOR DETERMINING CRITICAL DIMENSION VARIATION IN A LINE STRUCTURE

(75) Inventor: Marilyn I. Wright, Austin, TX (US)

(73) Assignee: Advanced Micro Devices, Inc., Austin, TX (US)

(*) Notice: Subject to any disclaimer, the term of this patent is extended or adjusted under 35 U.S.C. 154(b) by 205 days.

(21) Appl. No.: 09/897,624

(22) Filed: Jul. 2, 2001

(51) Int. Cl.$^7$ .............................................. H01L 21/66
(52) U.S. Cl. ...................................................... 438/16
(58) Field of Search ......................... 438/16, FOR 101, 438/FOR 142; 257/E21.53

(56) References Cited

U.S. PATENT DOCUMENTS

| | | | |
|---|---|---|---|
| 4,408,884 A | * 10/1983 | Kleinknecht et al. ........ 356/496 |
| 5,393,624 A | 2/1995 | Ushijima |
| 5,867,276 A | 2/1999 | McNeil et al. |
| 5,880,838 A | 3/1999 | Marx et al. |
| 5,963,329 A | * 10/1999 | Conrad et al. ............... 356/613 |
| 6,051,348 A | 4/2000 | Marinaro et al. |
| 6,245,584 B1 | 6/2001 | Marinaro et al. |
| 6,483,580 B1 | * 11/2002 | Xu et al. ..................... 356/300 |
| 6,556,652 B1 | * 4/2003 | Mazor et al. |
| 2002/0035455 A1 | * 3/2002 | Niu et al. ........................ 703/4 |
| 2002/0072001 A1 | * 6/2002 | Brown et al. .................. 430/30 |
| 2002/0090744 A1 | * 7/2002 | Brill et al. ...................... 438/11 |
| 2002/0113966 A1 | * 8/2002 | Shchegrov et al. ......... 356/369 |
| 2002/0149782 A1 | * 10/2002 | Raymond .................... 356/616 |
| 2002/0155629 A1 | * 10/2002 | Fairbairn et al. ............. 438/14 |
| 2002/0192966 A1 | * 12/2002 | Shanmugasundram et al. ........................... 438/692 |

OTHER PUBLICATIONS

Bishop et al., "Use of Scatterometry for resist process control," *SPIE Integrated Circuit Metrology, Inspection and Process Control*, 1673:441–452, 1992.
Hickman et al., "Use of diffracted light from latent images to improve lithography control," *SPIE Integrated Circuit Metrology, Inspection and Process Control*, 1464:245–257, 1991.

(List continued on next page.)

*Primary Examiner*—George Fourson
(74) *Attorney, Agent, or Firm*—Williams, Morgan & Amerson (57) ABSTRACT

A method for determining critical dimension variation includes providing a wafer having a grating structure comprising a plurality of lines; illuminating at least a portion of the lines with a light source; measuring light reflected from the illuminated portion of the lines to generate a reflection profile; and determining a critical dimension variation measurement of the lines based on the reflection profile. A metrology tool adapted to receive a wafer having a grating structure comprising a plurality of lines includes a light source, a detector, and a data processing unit. The light source is adapted to illuminate at least a portion of the lines. The detector is adapted to measure light reflected from the illuminated portion of the lines to generate a reflection profile. The data processing unit is adapted to determine a critical dimension variation measurement of the lines based on the reflection profile.

26 Claims, 6 Drawing Sheets

OTHER PUBLICATIONS

McNeil et al., "Scatterometry applied to microelectronics processing—Part 1," *Solid State Technology*, 37(3):29–56, 1993.

Miller and Mellicamp, "Development of an end–point detection procedure for the post–exposure bake process," *Integrated circuit metrology, inspection, and process control LX: 20–22, Feb., 1995, Santa Clara, California, SPIE Integrated Circuit Metrology, Inspection and Process Control*, 2439:78–88, 1995.

Milner et al., "Latent image exposure monitor using scatterometry," *SPIE Integrated Circuit Metrology, Inspection and Process Control*, 1673:274–283, 1992.

Prins et al., "Scatterometric sensor for PEB process control," *Metrology, inspection, and process control for microlithogtaphy, X:11–13, Mar., 1996, Santa Clara, California, SPIE Integrated Circuit Metrology, Inspection and Process Control*,2725:710–719, 1996.

Raymond et al., "Multiparameter process metrology using scatterometry," In: *Optical characterization techniques for high–performance microelectronic device manufacturing II, SPIE—The International Society for Optical Engineering*, 2638:84–93, Austin, Texas, Oct. 25–26, 1995.

Raymond et al., "Scatterometric sensor for lithography," In: *Manufacturing process control for microelectronic devices and circuits, SPIE—The International Society for Optical Engineering*, 2336:37–49, Austin, Texas, Oct. 20–21, 1994.

Sturtevant et al., "Post–exposure bake as a process–control parameter for chemically–amplified photoresist," *Metrology, inspection, and process control for microlithogtaphy, VII:2–4, Mar., 1993, Santa Jose, California, SPIE Integrated Circuit Metrology, Inspection and Process Control*, vol. 1926, 1993.

Sturtevant et al., "Use of scatterometric latent image detector in closed loop feedback control of linewidth," *SPIE Integrated Circuit Metrology, Inspection and Process Control*, 2196:352–359, 1994.

\* cited by examiner

METHOD AND APPARATUS FOR DETERMINING CRITICAL DIMENSION VARIATION IN A LINE STRUCTURE

BACKGROUND OF THE INVENTION

1. Field of the Invention

This invention relates generally to the field of semiconductor device manufacturing and, more particularly, to a method and apparatus for determining critical dimension variation in a line structure.

2. Description of the related art

Semiconductor integrated circuit devices are employed in numerous applications, including microprocessors. Generally, the performance of a semiconductor device is dependent on both the density and the speed of the devices formed therein. A common element of a semiconductor device that has a great impact on its performance is a transistor. Design features, such as gate length and channel length, are being steadily decreased in order to achieve higher package densities and to improve device performance. The rapid advance of field effect transistor design has affected a large variety of activities in the field of electronics in which the transistors are operated in a binary switching mode. In particular, complex digital circuits, such as microprocessors and the like, demand fast-switching transistors. Accordingly, the distance between the drain region and the source region of a field effect transistor, commonly referred to as the channel length or gate length dimension, has been reduced to accelerate the formation of a conductive channel between a source and a drain electrode as soon as a switching gate voltage is applied and, moreover, to reduce the electrical resistance of the channel.

A transistor structure has been created where the longitudinal dimension of the transistor, commonly referred to as the width dimension, extends up to 20 µm, whereas the distance of the drain and source, i.e., the gate length, may be reduced down to 0.2 µm or less. As the gate length of the channel has been reduced to obtain the desired switching characteristic of the source-drain line, the length of the gate electrode is also reduced. Since the gate electrode is typically contacted at one end of its structure, the electrical charges have to be transported along the entire width of the gate electrode, i.e., up to 20 µm, to uniformly build up the transverse electric field that is necessary for forming the channel between the source and drain regions. Due to the small length of the gate electrode, which usually consists of polycrystalline silicon, the electrical resistance of the gate electrode is relatively high, and it may cause high RC-delay time constants. Hence, the transverse electrical field necessary for fully opening the channel is delayed, thereby further deteriorating the switching time of the transistor. As a consequence, the rise and fall times of the electrical signals are increased, and the operating frequency, i.e., the clock frequency, may be adversely affected.

Figure 1A:
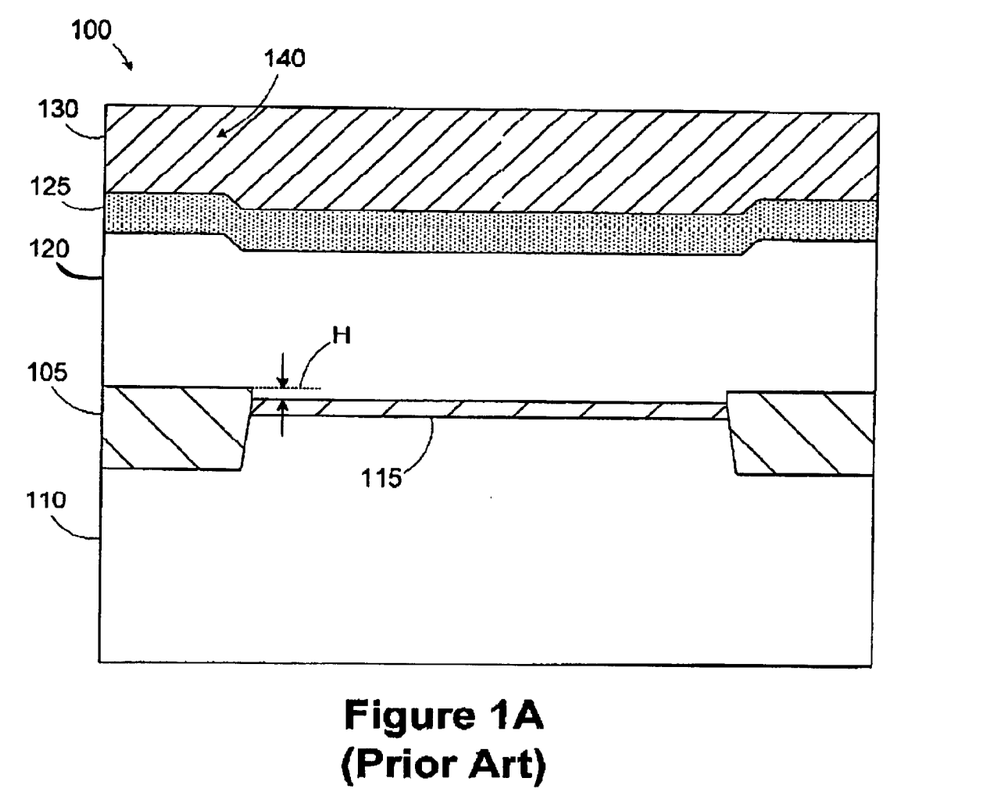
FIG. 1A is a cross section view of an exemplary semiconductor device.
Figure 1B:
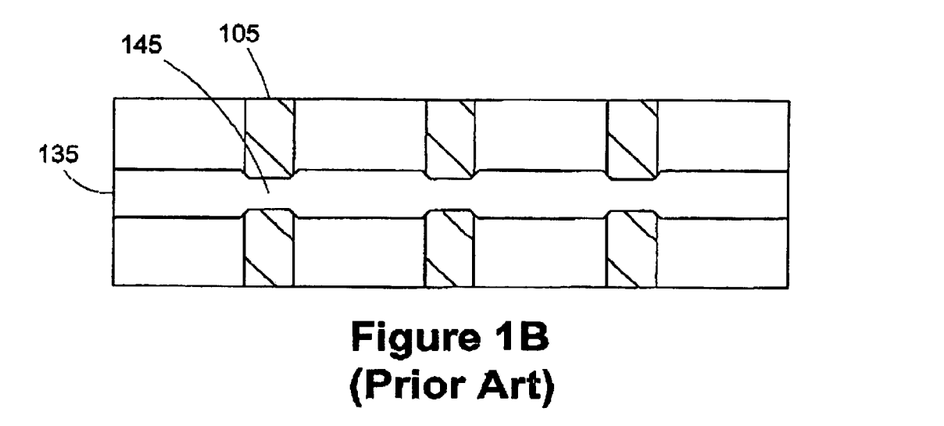
FIG. 1B is a top view of the device of FIG. 1A following formation of a gate electrode.

Transistors are formed through a series of steps. An exemplary transistor structure 100 is described in reference to FIGS. 1A and 1B. Initially, shallow trench isolation regions 105 are formed in a substrate 110 by etching trenches into the substrate 110 and, thereafter, filling the trenches with an appropriate insulating material (e.g., silicon dioxide). Next, a gate insulation layer 115 is formed over the substrate 110 between the trench isolation regions 105. This gate insulation layer 115 may be comprised of a variety of materials, but it is typically comprised of a thermally grown layer of silicon dioxide. Thereafter, a polysilicon gate electrode layer 120 is formed above the gate insulation layer 115. An antireflective coating (ARC) layer 125 may be formed over the polysilicon layer 120 to minimize notches caused by reflections during subsequent photolithographic techniques. A photoresist layer 130 is formed over the ARC layer 125 and patterned to form a mask for etching gate electrodes 135 as seen in FIG. 1B, a top view of the transistor structure 100 of FIG. 1A. Of course, millions of such gate electrodes 135 may be formed across the entire surface of the substrate 110 during this patterning process.

The gate electrode 135 passes over isolation structures 105 associated with adjacent transistor structures. The isolation structures 105 are typically not flush with respect to the surface of the substrate 11 O. The distance that the isolation structures 105 extend beyond the surface of the substrate 110 may be referred to as the step height, H, of the isolation structures 105. In regions 140 where the photoresist layer 130 passes over the isolation structures 105, its thickness may be reduced due to the step height of the isolation structures 105. When the photoresist layer 130 is subsequently exposed in a stepper to form the mask pattern, the reduced thickness regions 140 receive an effectively higher exposure dose due to the reduced thickness, resulting in a wider pattern in the exposed portions. The exposed portions of the photoresist layer 130 are removed and the remaining portions are used as a pattern for etching the gate electrodes 135. The remaining portions have a narrower pattern in the reduced thickness regions 140. Thus, when the gate electrodes 135 are subsequently etched, they also have narrower portions 145 in the regions overlying the isolation structures 105.

The width variation across the length of the gate electrodes 135 described above may be referred to as a critical dimension (CD) variation. In modem integrated circuit devices, a plurality of gate electrodes 135 may be formed adjacent one another, separated by a defined pitch. CD variation effectively reduces the width of the gate electrodes 135. A subsequently formed interlayer dielectric (ILD) layer (not shown) is formed over the transistor structures 100 and between the gate electrodes 135 to insulate them from one another. Device designers must take into account the potential magnitude of the CD variation in designing the layout of the transistors 100 to ensure the insulating ability of the ILD layer and the conductive ability of the gate electrodes 135.

The present invention is directed to overcoming, or at least reducing the effects of, one or more of the problems set forth above.

SUMMARY OF THE INVENTION

One aspect of the present invention is seen in a method for determining critical dimension variation. The method includes providing a wafer having a grating structure comprising a plurality of lines; illuminating at least a portion of the lines with a light source; measuring light reflected from the illuminated portion of the lines to generate a reflection profile; and determining a critical dimension variation measurement of the lines based on the reflection profile.

Another aspect of the present invention is seen in a metrology tool adapted to receive a wafer having a grating structure comprising a plurality of lines. The metrology tool includes a light source, a detector, and a data processing unit. The light source is adapted to illuminate at least a portion of the lines. The detector is adapted to measure light reflected from the illuminated portion of the lines to generate a reflection profile. The data processing unit is adapted to determine a critical dimension variation measurement of the lines based on the reflection profile.

BRIEF DESCRIPTION OF THE DRAWINGS

The invention may be understood by reference to the following description taken in conjunction with the accompanying drawings, in which like reference numerals identify like elements, and in which.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claims.

DETAILED DESCRIPTION OF SPECIFIC EMBODIMENTS

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

Figure 2:
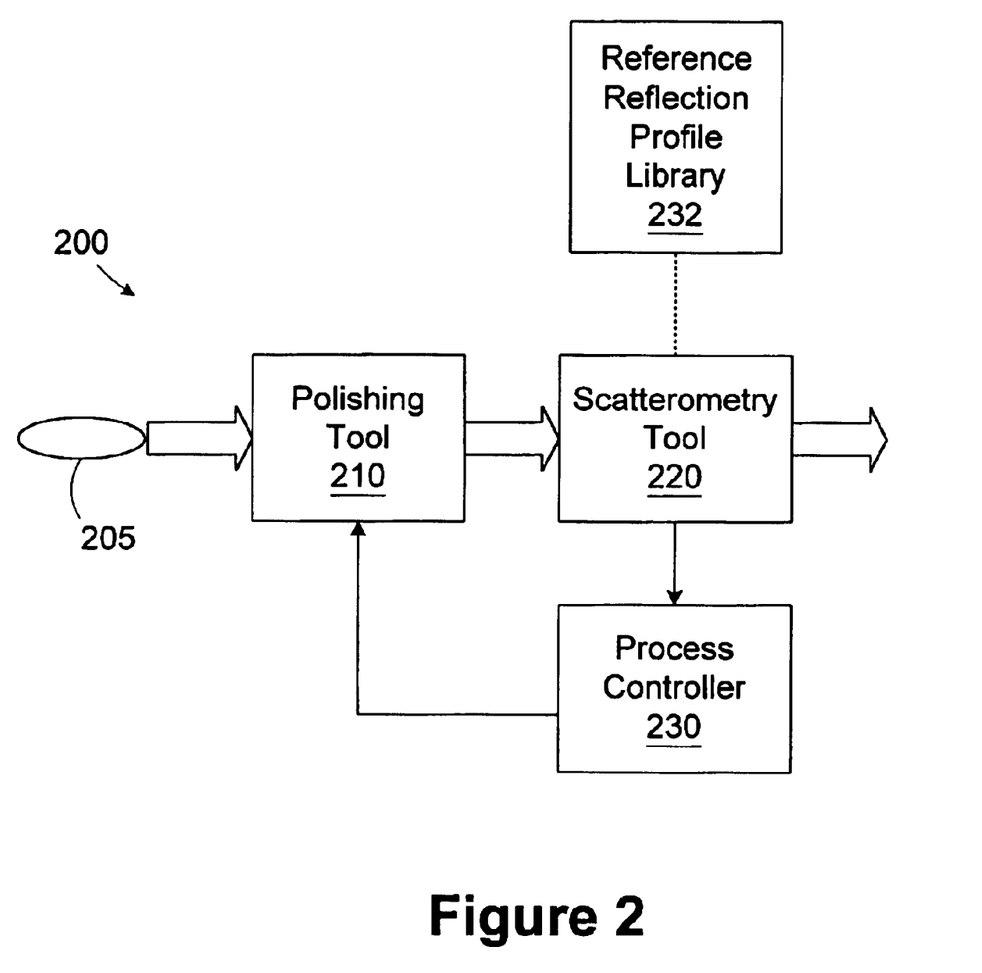
FIG. 2 is a simplified diagram of an illustrative processing line for processing wafers in accordance with one illustrative embodiment of the present invention.

Referring to FIG. 2, a simplified diagram of an illustrative processing line 200 for processing wafers 205 in accordance with one illustrative embodiment of the present invention is provided. The processing line 200 includes a polishing tool 210 for polishing the wafers 205 in accordance with a polishing recipe. The polishing tool 210 may be used to polish process layers formed on the wafer 205, such as a silicon dioxide layer used to form an isolation structure, as described above for the isolation structures 105 of FIGS. 1A and 1B.

The processing line 200 includes a scatterometry tool 220 adapted to measure critical dimension (CD) variation in a line structure (e.g., a gate electrode) formed on the wafer 205. In general, the scatterometry tool 220 includes optical hardware, such as an ellipsometer or reflectometer, and a data processing unit loaded with a scatterometry software application for processing data collected by the optical hardware. For example, the optical hardware may include a model OP5230 or OP5240 with a spectroscopic ellipsometer offered by ThermaWave, Inc. of Freemont Calif. The data processing unit may comprise a profile application server manufactured by Timbre Technologies, a subsidiary of Tokyo Electron Limited, Inc. of Tokyo, Japan and distributed by Therma-Wave, Inc. The scatterometry tool 220 may be external to the polishing tool 210 or, alternatively, the scatterometry tool 220 may be installed in an in-situ arrangement.

A process controller 230 is provided for providing feedback to the polishing tool 210 based on the CD variation measured by the scatterometry tool 220. The process controller 230 adjusts its operating recipe to improve the uniformity of the polishing process and reduce the step height for subsequently polished wafers 205.

In the illustrated embodiment, the process controller 230 is a computer programmed with software to implement the functions described. However, as will be appreciated by those of ordinary skill in the art, a hardware controller designed to implement the particular functions may also be used. Moreover, the functions performed by the process controller 230, as described herein, may be performed by multiple controller devices distributed throughout a system. Additionally, the process controller 230 may be a stand-alone controller, it may be integrated into a tool, such as the polishing tool 210 or the scatterometry tool 220, or it may be part of a system controlling operations in an integrated circuit manufacturing facility.

Portions of the invention and corresponding detailed description are presented in terms of software, or algorithms and symbolic representations of operations on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" or "displaying" or the like, refer to the action and processes of a computer system, or similar electronic computing device, that manipulates and transforms data represented as physical, electronic quantities within the computer system's registers and memories into other data similarly represented as physical quantities within the computer system memories or registers or other such information storage, transmission or display devices.

An exemplary software system capable of being adapted to perform the functions of the process controller 230, as described, is the Catalyst system offered by KLA-Tencor, Inc. The Catalyst system uses Semiconductor Equipment and Materials International (SEMI) Computer Integrated Manufacturing (CIM) Framework compliant system technologies and is based on the Advanced Process Control (APC) Framework. CIM (SEMI E81-0699-Provisional Specification for CIM Framework Domain Architecture) and APC (SEMI E93-0999 -Provisional Specification for CIM Framework Advanced Process Control Component) specifications are publicly available from SEMI.

In one embodiment, the scatterometry tool 220 measures CD variation on features formed in the production devices. In some cases, the geometry of the features or the presence of underlying structures may inhibit scatterometry measurements. Accordingly, test structures having the same general configuration as features formed on the wafer 205 may be employed. The test structures may be formed in a region of the wafer 205 not normally used for forming devices (e.g., in the periphery region where identification codes are typically scribed or in the scribe lines between production die).

Figure 3:
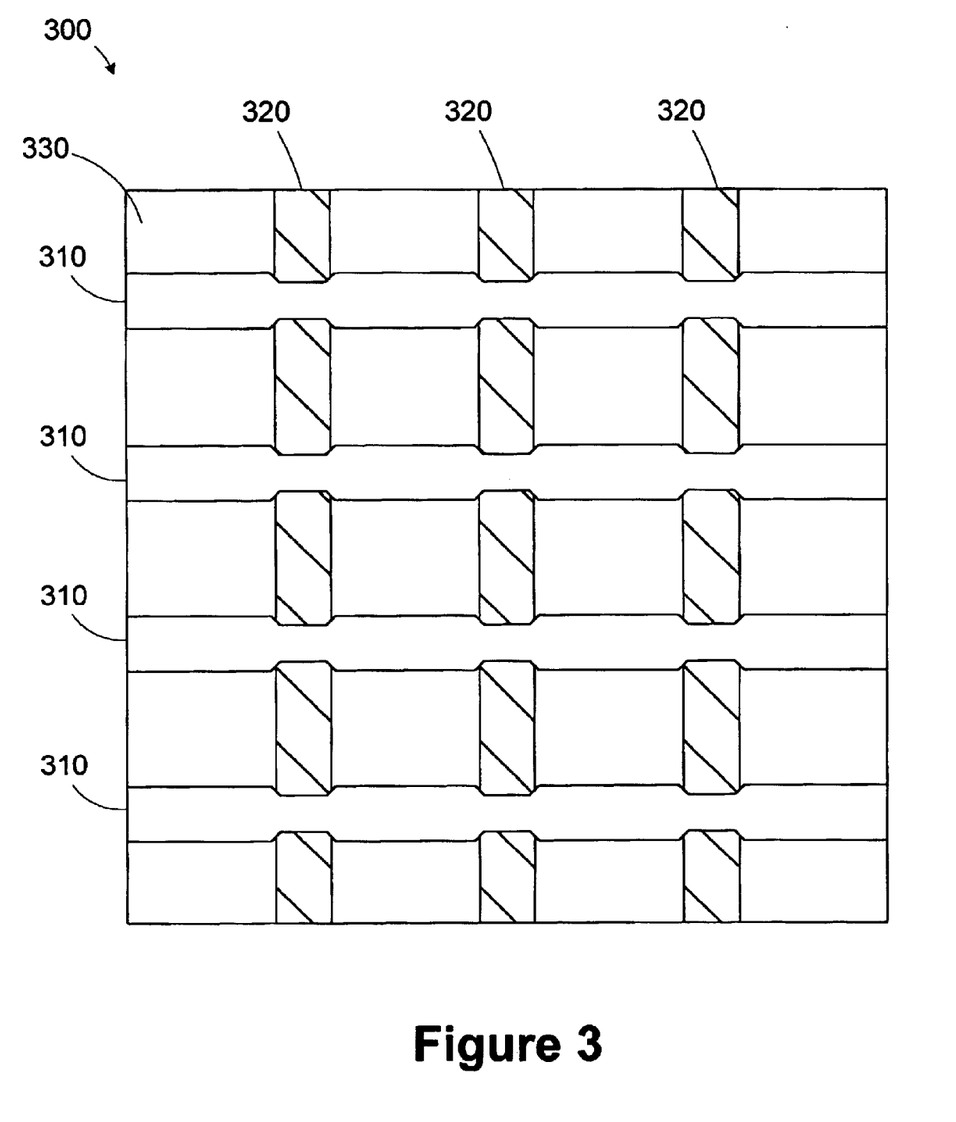
FIG. 3 is a top view of an exemplary semiconductor device including a test grating structure.

Referring briefly to FIG. 3, an exemplary grating structure 300 that may used as a test structure on the wafer 205 is shown. The grating structure 300 has the same general construction (e.g., geometry, materials, etc.) as features included in the devices formed on the wafer 205. In the illustrated embodiment, the grating structures 300 includes lines 310 passing over isolation structures 320 formed in a substrate 330. A variety of isolation structures 320 may be provided with different widths and pitches (i.e., to provide features with different step heights) depending on the different features present in an actual device. In general, the lines 310 will exhibit an increased CD variation over the isolation structures 320 with a greater step height.

Figure 4:
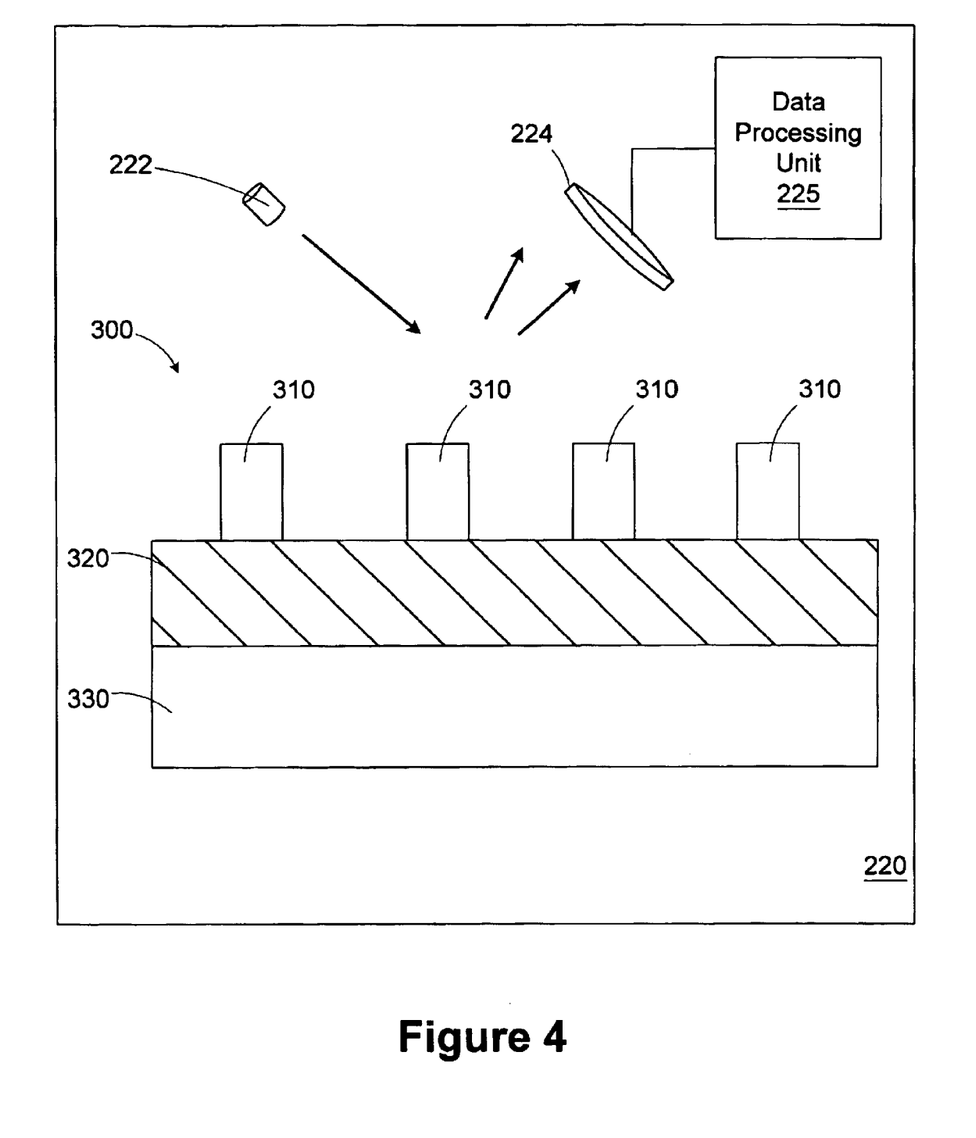
FIG. 4 is a simplified view of the scatterometry tool of FIG. 2 loaded with the test structure of FIG. 3.

Turning now to FIG. 4, a simplified view of the scatterometry tool 220 loaded with a wafer 205 having the grating structure 300 of FIG. 3 is provided. Although the scatterometry tool 220 is described as it may be used to measure CD variation on a test structure, it may also be employed to measure CD variation in a production device. The scatterometry tool 220, includes a light source 222 and a detector 224 positioned proximate the grating structure 300. The light source 222 of the scatterometry tool 220 illuminates at least a portion of the grating structure 300, and the detector 224 takes optical measurements, such as intensity or phase, of the reflected light. A data processing unit 225 receives the optical measurements from the detector 224 and processes the data to identify CD variation in the lines 310.

The scatterometry tool 220 may use monochromatic light, white light, or some other wavelength or combinations of wavelengths, depending on the specific implementation. The angle of incidence of the light may also vary, depending on the specific implementation. The light analyzed by the scatterometry tool 220 typically includes a reflected component (i.e., incident angle equals reflected angle) and a refracted component (i.e., incident angle does not equal the reflected angle). For purposes of discussion here, the term "reflected" light is meant to encompass both components.

CD variations in the lines 310 cause changes in the reflection profile (e.g., intensity vs. wavelength–$\tan(\delta)$, phase vs. wavelength–$\sin(\Psi)$, where $\delta$ and $\Psi$ are common scatterometry outputs known to those of ordinary skill in the art) measured by the scatterometry tool 220 as compared to the light scattering profile that would be present in lines 310 having little or no CD variation, or at least acceptable amounts of CD variation.

Figure 5A:
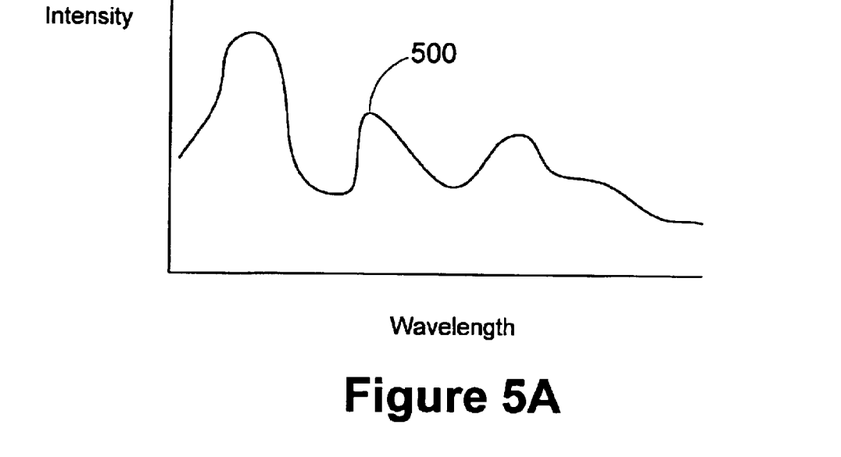
FIGS. 5A, 5B, and 5C illustrate a library of exemplary scatterometry curves used to characterize the wafer measured in the scatterometry tool of FIG. 4.
Figure 5B:
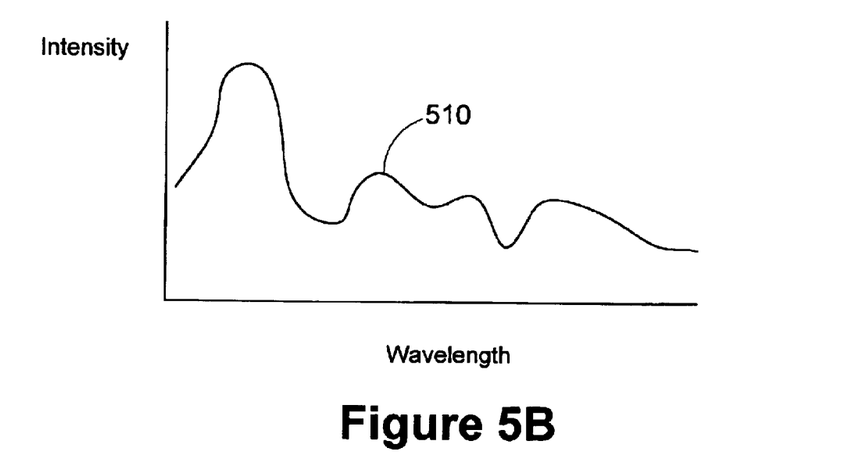
Figure 5C:
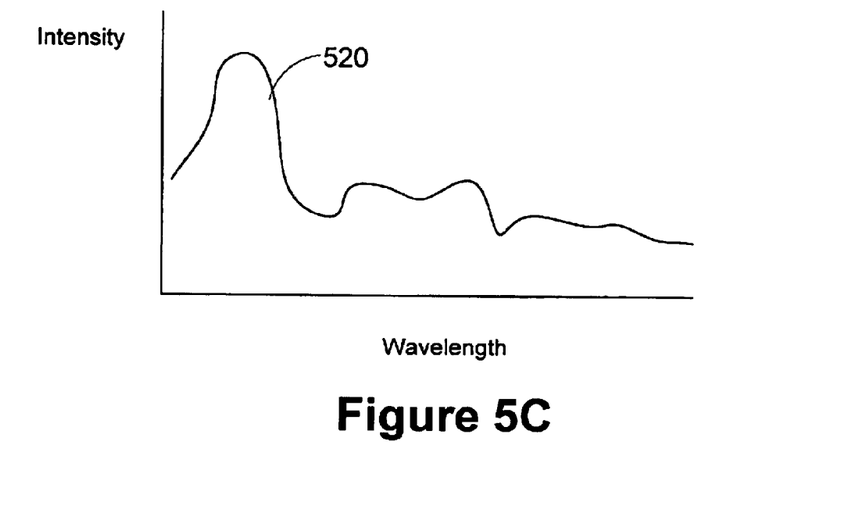

FIGS. 5A, 5B, and 5C illustrate exemplary reflection profiles 500, 510, 520 that may be included in a reference reflection profile library 232 (see FIG. 2) used by the data processing unit 225 to characterize the CD variation of the lines 310 based on the reflection profiles measured by the scatterometry tool 220. The particular reflection profile expected for any structure depends on the specific geometry of the grating structure 300 and the parameters of the measurement technique employed by the scatterometry tool 220 (e.g., light bandwidth, angle of incidence, etc.). The profiles in the reference reflection profile library 232 are typically calculated theoretically by employing Maxwell's equations to model individual spectra based on the expected characteristics of the grating structure 300. Spectra are generated at a predetermined resolution for many, if not all, profiles that may be expected, and the sum of all said spectra constitute the reference reflection profile library 232. Scatterometry libraries are commercially available from Timbre Technologies, Inc. The profiles in the reference reflection profile library 232 may also be generated empirically by measuring reflection profiles of sample wafers and subsequently characterizing the measured wafers by destructive or non-destructive examination techniques.

The reflection profile 500 of FIG. 5A represents an expected profile for a grating structure 300 having lines 310 with essentially no CD variation. The reflection profile 510 of FIG. 5B represents an expected profile for a grating structure 300 having lines 310 that exhibit a moderate amount of CD variation. The reflection profile 520 of FIG. 5C represents an expected profile for a grating structure 300 having lines 310 that exhibit a relatively high level of CD variation. The reflection profiles of grating structures 300 having lines 310 with varying amounts of CD variation may be included in the reference reflection profile library 232.

The data processing unit 225 receives a reflection profile measured by the detector 224 and compares it to the reference reflection profile library 232. Each reference profile has an associated CD variation metric related to the degree of CD variation. For example, the CD variation metric may comprise actual width measurements or a ratio of the CD variation as a percentage. The data processing unit 225 determines the reference reflection profile having the closest match to the measured reflection profile. Techniques for matching the measured reflection profile to the closest reference reflection profile are well known to those of ordinary skill in the art, so they are not described in greater detail herein.

In another embodiment, the process controller 230 or other external controller (not shown) may be adapted to compare the measured reflection profile to the reference reflection profile library 232. In such a case, the scatterometry tool 220 would output the matching reference reflection profile, and the process controller 230 may link that reference reflection profile to an associated CD variation metric.

In another embodiment, the measured reflection profile may be compared to a target reflection profile selected from the reference reflection profile library 232 for a grating structure 300 having lines 310 exhibiting a known and desired CD variation characteristic (e.g., no CD variation or minimal CD variation). For example, a target reflection profile may be calculated for a grating structure 300 having lines 310 with an ideal or acceptable CD variation using Maxwell's equations, and that target reflection profile may be stored in the reference reflection profile library 232. Thereafter, the measured reflection profile of a grating structure 300 with lines 310 having an unknown degree of CD variation is compared to the target reflection profile. Based upon this comparison, a relatively rough approximation of the CD variation may be determined. That is, by comparing the measured reflection profile to the target reflection profile, CD variation may be approximated, such that further matching of the measured reflection profile with additional reference reflection profiles from the reference reflection profile library 232 is unwarranted. Using this technique, an initial determination may be made as to the CD variation. Of course, this step may be performed in addition to the matching or correlating of a measured reflection profile to a reference reflection profile from the reference reflection profile library 232 as described above. The CD variation approximation may also be used as a fault detection signal, where a significant amount of CD variation may result in a later failure or unacceptable performance of the devices in subsequent electrical testing.

After receiving the CD variation metric from the scatterometry tool 220, the process controller 230 may take a variety of autonomous actions. The actions may include fault detection and/or process control functions. In one embodiment of the present invention, the process controller 230 is adapted to modify the operating recipe of the polishing tool 210 based on the CD variation metric to control polishing operations on subsequent wafers processed by the polishing tool 210. Because the CD variation is an indirect measure of step height, the process controller 230 may adjust the polishing recipe for subsequently polished wafers to control the step height. Recipe parameters, such as the polish time, downforce, polishing pad speed, etc., may be changed.

The process controller 230 may use a control model of the polishing tool 210 for changing its operating recipe. For example, the process controller 230 may use a control model relating the CD variation metric to a particular operating recipe parameter in the polishing tool 210 to control the polishing rate or polishing time to correct for any overpolishing. The control model may be developed empirically using commonly known linear or non-linear techniques. The control model may be a relatively simple equation based model (e.g., linear, exponential, weighted average, etc.) or a more complex model, such as a neural network model, principal component analysis (PCA) model, or a projection to latent structures (PLS) model. The specific implementation of the model may vary depending on the modeling technique selected.

CD variation models may be generated by the process controller 230, or alternatively, they may be generated by a different processing resource (not shown) and stored on the process controller 230 after being developed. The CD variation models may be developed using the polishing tool 210 or using a different tool (not shown) having similar operating characteristics. For purposes of illustration, it is assumed that the CD variation models are generated and updated by the process controller 230 or other processing resource based on the actual performance of the polishing tool 210 as measured by the scatterometry tool 220. The CD variation models may be trained based on historical data collected from numerous processing runs of the polishing tool 210.

The process controller 230 may also use the CD variation metric for fault detection. If the amount of CD variation measured is sufficient to significantly degrade the performance of the devices, the wafer may be scrapped or reworked prior to performing any additional process steps. The CD variation results may also be used by process and design engineers to change the design of the device. For example, if a particular structure is susceptible to CD variation that is difficult to correct by changing the operating recipe of the polishing tool 210, the structure may be redesigned (e.g., by changing the pitch, width, or layout) to reduce the susceptibility of the structure. A test structure with a wide array of space/pitch grating structures may be employed and measured to develop CD variation-driven design rules.

Figure 6:
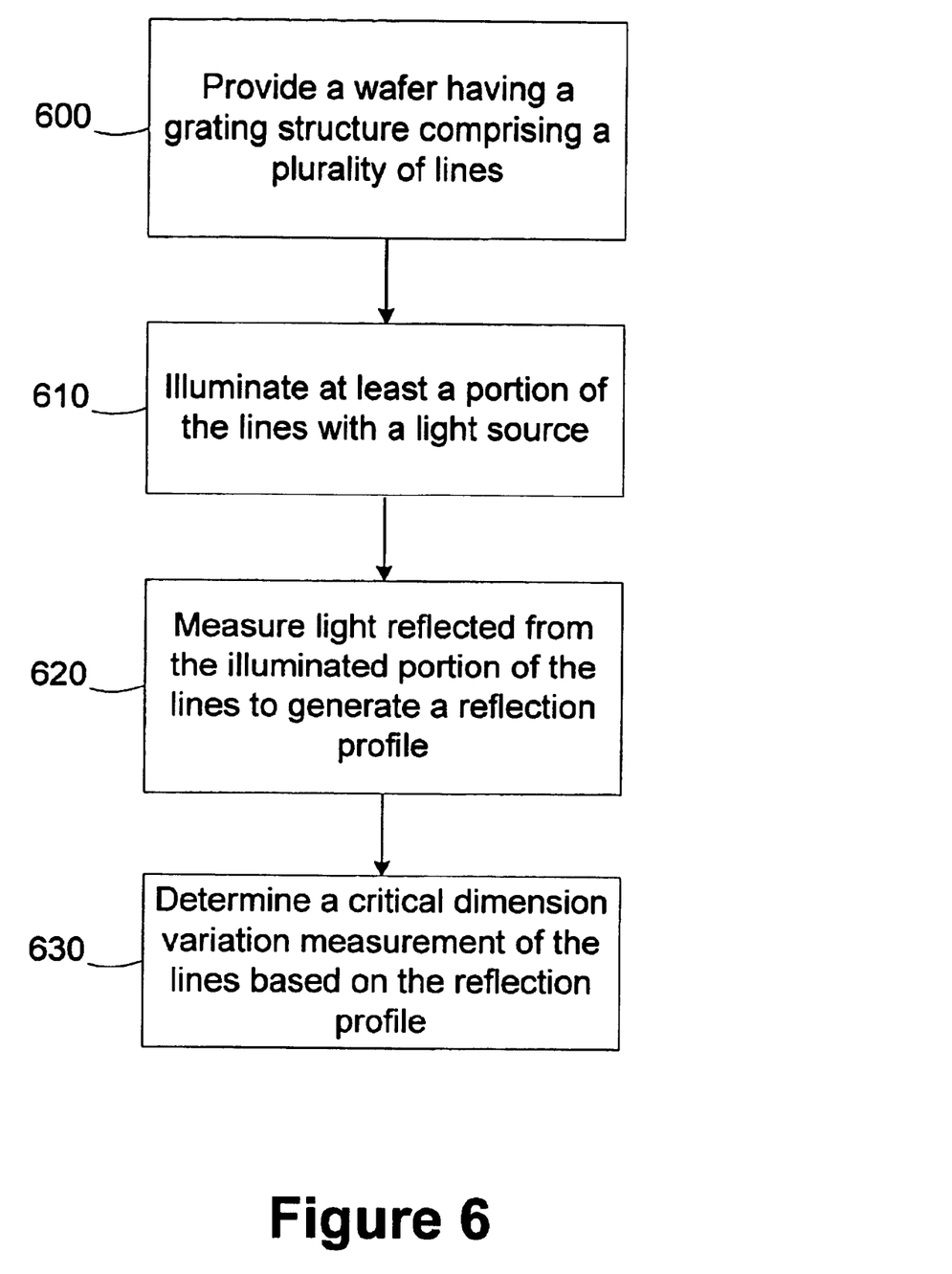
FIG. 6 is a simplified flow diagram of a method for determining critical dimension variation in accordance with another illustrative embodiment of the present invention.

FIG. 6 is a simplified flow diagram of a method for detecting CD variation in accordance with another illustrative embodiment of the present invention. In block 600, a wafer having a grating structure comprising a plurality of lines is provided. In block 610, at least a portion of the lines is illuminated with a light source. In block 620, light reflected from the illuminated portion of the lines is measured to generate a reflection profile. In block 630, a critical dimension variation measurement of the lines is determined based on the reflection profile.

Monitoring CD variation based on measurements from the scatterometry tool 220, as described above, has numerous advantages. The polishing tool 210 may be controlled to reduce the amount of CD variation encountered. Decreased CD variation reduces the likelihood that a device may be degraded or must be scrapped. Accordingly, the quality of the devices produced on the processing line 200 and the efficiency of the processing line 200 are both increased. Furthermore, CD variation analysis provided design engineers with feedback for redesigning features that are less susceptible to CD variation.

The particular embodiments disclosed above are illustrative only, as the invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular embodiments disclosed above may be altered or modified and all variations are considered within the scope and spirit of the invention. Accordingly, the protection sought herein is as set forth in the claims below.

What is claimed:

1. A method for determining critical dimension variation comprising:

providing a wafer having a grating structure comprising a plurality of lines;

illuminating at least a portion of the lines with a light source;

measuring light reflected from the illuminated portion of the lines to generate a reflection profile; and determining a critical dimension variation measurement along a length of the lines based on the reflection profile.

2. The method of claim 1, wherein determining the critical dimension variation measurement further comprises:

comparing the generated reflection profile to a library of reference reflection profiles, each reference reflection profile having an associated critical dimension variation metric;

selecting a reference reflection profile closest to the generated reflection profile; and determining the critical dimension variation measurement based on the critical dimension variation metric associated with the selected reference reflection profile.

3. The method of claim 1, further comprising determining at least one parameter of an operating recipe of a polishing tool adapted to polish a subsequent wafer based on the reflection profile.

4. The method of claim 3, wherein determining at least one parameter of the operating recipe of the polishing tool comprises changing at least one of a polish time, a downforce parameter, and a polishing pad speed parameter.

5. The method of claim 3, wherein determining the at least one parameter of the operating recipe further comprises determining the at least one parameter of the operating recipe for a polishing process to be performed on a shallow trench isolation region of the subsequent wafer.

6. The method of claim 1, wherein generating the reflection profile comprises generating the reflection profile based on at least one of intensity and phase of the reflected light.

7. The method of claim 1, wherein providing the wafer comprises providing the wafer having the grating structure formed in a test structure on the wafer.

8. The method of claim 1, wherein providing the wafer comprises providing the wafer having the grating structure formed in a production device on the wafer.

9. The method of claim 1, wherein determining the critical dimension variation measurement further comprises:

comparing the generated reflection profile to a target reflection profile; and determining the critical dimension variation measurement base on the comparison of the generated reflection profile and the target reflection profile.

10. The method of claim 1, further comprising identifying a fault condition associated with the lines based on the critical dimension variation measurement.

11. A method for determining critical dimension variation comprising:

providing a wafer having a grating structure comprising a plurality of lines;

illuminating at least a portion of the lines with a light source;

measuring light reflected from the illuminated portion of the lines to generate a reflection profile; and comparing the generated reflection profile to a library of reference reflection profiles, each reference reflection profile having an associated critical dimension variation metric;

selecting a reference reflection profile closest to the generated reflection profile; and determining a critical dimension variation measurement along a length of the lines based on the critical dimension variation metric associated with the selected reference reflection profile.

12. The method of claim 11, further comprising determining at least one parameter of an operating recipe of a polishing tool adapted to polish a subsequent wafer based on the reflection profile.

13. The method of claim 12, wherein determining at least one parameter of the operating recipe of the polishing tool comprises changing at least one of a polish time, a downforce parameter, and a polishing pad speed parameter.

14. The method of claim 12, wherein determining the at least one parameter of the operating recipe further comprises determining the at least one parameter of the operating recipe for a polishing process to be performed on a shallow trench isolation region of the subsequent wafer.

15. The method of claim 11, wherein generating the reflection profile comprises generating the reflection profile based on at least one of intensity and phase of the reflected light.

16. The method of claim 11, wherein providing the wafer comprises providing the wafer having the grating structure formed in a test structure on the wafer.

17. The method of claim 11, wherein providing the water comprises providing the wafer having the grating structure formed in a production device on the wafer.

18. The method of claim 11, further comprising identifying a fault condition associated with the lines based on the critical dimension variation measurement.

19. A method for determining critical dimension variation, comprising:

providing a wafer having a grating structure comprising a plurality of lines;

illuminating at least a portion of the lines with a light source;

measuring light reflected from the illuminated portion of the lines to generate a reflection profile; and comparing the generated reflection profile to a target reflection profile; and determining a critical dimension variation measurement along a length of the lines based on the comparison of the generated reflection profile and the target reflection profile.

20. The method of claim 19, further comprising determining at least one parameter of an operating recipe of a polishing tool adapted to polish a subsequent wafer based on the reflection profile.

21. The method of claim 20, wherein determining at least one parameter of the operating recipe of the polishing tool comprises changing at least one of a polish time, a downforce parameter, and a polishing pad speed parameter.

22. The method of claim 20, when determining the at least one parameter of the operating recipe further comprises determining the at least one parameter of the operating recipe for a polishing process to be performed on a shallow trench isolation region of the subsequent wafer.

23. The method of claim 19, wherein generating the reflection profile comprises generating the reflection profile based on at least one of intensity and phase of the reflected light.

24. The method of claim 19, wherein providing the wafer comprises providing the wafer having the grating structure formed in a test structure on the wafer.

25. The method of claim 19, wherein providing the wafer comprises providing the wafer having the grating structure formed in a production device on the wafer.

26. The method of claim 19, further comprising identifying a fault condition associated with lines based on the critical dimension variation measurement.

* * * * *